United States Patent [19]

Tomotsu et al.

[11] Patent Number: 5,070,160

[45] Date of Patent: Dec. 3, 1991

[54] PROCESS FOR DRYING ALUMINOXANE AND PROCESS FOR PRODUCING POLYMERS

[75] Inventors: Norio Tomotsu; Hiroshi Maezawa; Koji Yamamoto, all of Ichihara, Japan

[73] Assignee: Idemitsu Kosan Co., Ltd., Tokyo, Japan

[21] Appl. No.: 514,420

[22] Filed: Apr. 25, 1990

[30] Foreign Application Priority Data

May 25, 1989 [JP] Japan .................................. 1-130253

[51] Int. Cl.$^5$ ............................................. C08F 4/642
[52] U.S. Cl. ..................................... 526/165; 526/159; 502/8; 502/9; 502/103; 556/179; 34/14
[58] Field of Search ...................... 526/159, 165, 346; 556/179; 34/14; 502/8, 9, 103

[56] References Cited

U.S. PATENT DOCUMENTS

| | | | |
|---|---|---|---|
| 4,680,353 | 7/1987 | Ishihara et al. | 526/160 |
| 4,772,736 | 9/1988 | Edwards et al. | 556/179 |
| 4,952,540 | 8/1990 | Kioka et al. | 526/904 X |

*Primary Examiner*—Fred Teskin
*Attorney, Agent, or Firm*—Frishauf, Holtz, Goodman & Woodward

[57] ABSTRACT

Disclosed is a process for drying aluminoxane, which comprises drying a viscous solution containing aluminoxane, while applying a shearing force sufficient to keep said viscous solution in polydispersive state, so as to make the solution to be a solid-state polydispersoid. Also disclosed is a process for producing a polymer which comprises polymerizing a polymerizable monomer, using the aluminoxane obtained by the process of the present invention.

According to the process of the present invention, aluminoxane in uniform powder which is easy to treat can be efficiently obtained in an industrial scale, and polymers can be produced at high efficiency.

11 Claims, 4 Drawing Sheets

40

50

PROCESS FOR DRYING ALUMINOXANE AND PROCESS FOR PRODUCING POLYMERS

BACKGROUND OF THE INVENTION

1. Field of the Invention

The present invention relates to a process for drying aliminoxane and a process for producing polymers, and more particularly, it relates to a process for obtaining aluminoxane which is used as a catalyst in polymerization of polymerizable monomers, in a state suitable for use as a catalyst.

2. Description of the Related Arts

Aluminoxane is usually obtained from an organoaluminum compound such as trialkylaluminum as the starting material, and it results in a solution diluted with a large amount of organic solvents containing unreacted organoaluminum. Accordingly, a drying step for removing said organoaluminum and the organic solvents is required at the last stage. However, if the resulting aluminoxane solution is heated to dryness without any treatment, it evaporates into a glassy solid state, through a state of highly viscous solution. Therein a large amount of power is required to reach such a dryness, and a uniform drying is difficult.

As the catalyst for production of polymers, aluminoxane is desired to be in powder form, which is easy to dissolve. To obtain aluminoxane powder, however, only the spray-drying method and the solvent deposition method have been known.

Said spray-drying method requires a large amount of inert gas, accompanies a considerable amount of aluminoxane losses, and gives a poor yield. The solvent deposition method requires a large amount of solvent, and in addition, another step for removing solvents.

According to these methods, further, the resulting aluminoxane sometimes contains residual trialkylaluminum in a large amount, and it was difficult to obtain an aluminoxane of high quality.

SUMMARY OF THE INVENTION

An object of the present invention is to provide a process for producing aluminoxane, according to which the viscous solution of aluminoxane after preparation is easily dried, and aluminoxane powder of improved quality results in a high yield.

Another object of the invention is to provide a process for producing an aluminoxane in a state suitable to be used as a catalyst for production of polymer.

The present invention provides a process for drying aluminoxane, which comprises drying a viscous solution containing aluminoxane while providing a shearing force sufficient to keep said viscous solution in a polydispersive state, so as to make a solid-state polydispersoid substantially.

Figure 1:
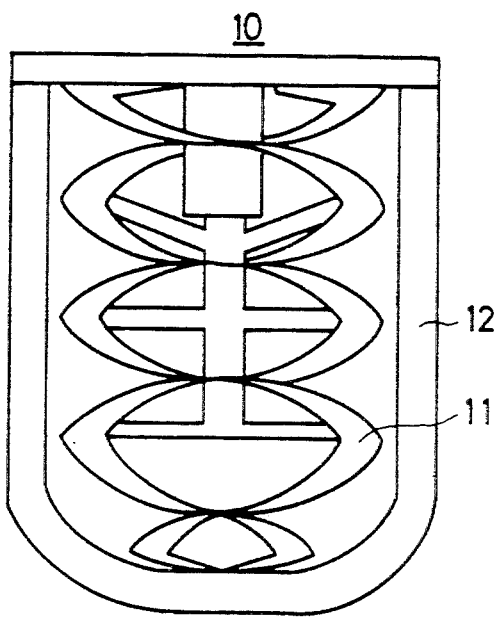
FIG. 1 is an illustration of a dryer provided with a double helical ribbon blade.

10, 20, 30, 40, 50:dryers,
11:double helical ribbon blade,
12:heating jacket,
21:screw-type agitating blade which rotates about its own axis while also orbiting around the center axis of the conical tank,
22:heating jacket,
23:swing arm,
31:rotating blade,
32:jacket,
33:drying chamber,
34:heat-transfer blade,
35:inlet,
36:outlet,
41:paddle,
42:heating jacket,
43 inlet,
44:outlet,
51 inlet,
52 grinding part,
53:inlet for hot air,
54:classifying part,
55:outlet

DESCRIPTION OF THE PREFERRED EMBODIMENTS

Aluminoxanes desired in the present invention are, for example, chain alkylaluminoxanes represented by the general formula:

$$R^1 \diagdown_{R^1} Al-O \left( Al-O \right)_n Al \diagup^{R^1}_{R^1}$$
$$\quad \quad \quad \quad \quad \; \; |$$
$$\quad \quad \quad \quad \quad R^1$$

wherein $R^1$ indicates an alkyl group having 1 to 8 carbon atoms, and n indicates polymerization degree, and cycloalkylaluminoxanes having a repeating unit represented by the general formula:

$$\left( Al-O \right)$$
$$\; \; |$$
$$\; R^1$$

wherein $R^1$ is as defined above.

These aluminoxanes are usually prepared by contacting an organoaluminum compound represented by the general formula:

$$AlR^1_3$$

(wherein $R^1$ is as defined above) and a condensing agent. Specific examples of these organoaluminum compounds are trialkylaluminums including trimethylaluminum, triethylaluminum, triisobutylaluminum, and tributylaluminum.

A typical example of the condensing agent is water. In addition, any compounds capable of undergoing a condensation reaction with organoaluminum compounds can be used.

The reaction of the organoaluminum compound and water is not specified, but can be performed according to known methods; for example, (1)a method in which an organoaluminum compound is dissolved in an organic solvent and then contacted with water or steam;

(2) a method in which water is dissolved in an organic solvent, and then an organoaluminum compound is added; and (3) a method in which an organoaluminum compound is reacted with water of crystallization contained in metal salts and the like, or water adsorbed on inorganic or organic compounds.

Generally, the reaction product of organoaluminum compounds such as trialkylaluminum and water includes the abovementioned chain alkylaluminoxane and cycloalkylaluminoxane, unreacted trialkylaluminum, a mixture of various condensation products, and further complicatedly associated molecules thereof, which become various products according to the contacting conditions of trialkylaluminum and water. According to these methods, aluminoxane is obtained in the state of a solution diluted with an organic solvent containing unreacted organoaluminum compounds, as described above.

In the process for drying aluminoxane in the present invention, the aluminoxane solution obtained in such a state is dried, while a shearing force sufficient to keep it to be polydispersive is applied, so as to be substantially a solid-state polydispersoid.

As the means to effect drying so that the reaction product may be substantially a solid-state polydispersoid, while providing a shearing force sufficient to keep it in a polydispersive state, as described above, various dryers can be used. Specific examples of dryers are illustrated in the drawings.

FIG. 1 illustrates dryer 10 provided with a double helical ribbon blade 11. Said dryer 10 is capable of heating Material (material to be dried) to a prescribed temperature, by supplying a proper heating fluid such as steam to the heating jacket 12 surrounding the container, while applying prescribed shearing force to Material by use of the double helical ribbon blade 11.

Figure 2:
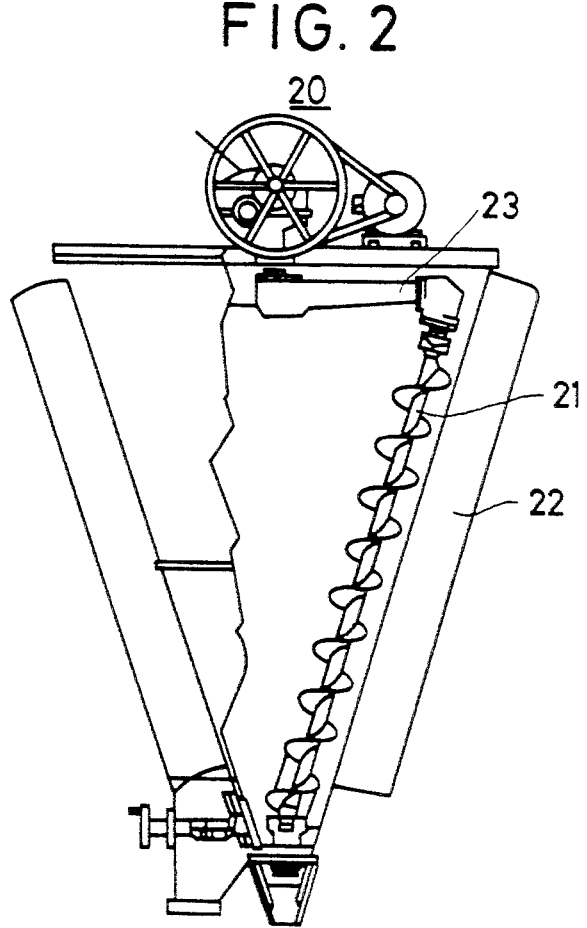
FIG. 2 is an illustration of a dryer of Nauta mixer provided with a screw-type agitating blade which rotates about its own axis while also orbiting around the center axis of the conical tank.

FIG. 2 shows a dryer 20 of Nauta mixer type, provided with a rotating screw-type agitating blade 21 orbiting in a conical tank. In said dryer 20, agitating blade 21 provided at the end of the swing arm 23 is revolved and rotated by the swing arm 23, to obtain a prescribed shearing force. Said dryer 20 can heat Material to a prescribed temperature, by supplying a heating fluid to the heating jacket 22 surrounding the container.

Figure 3A:
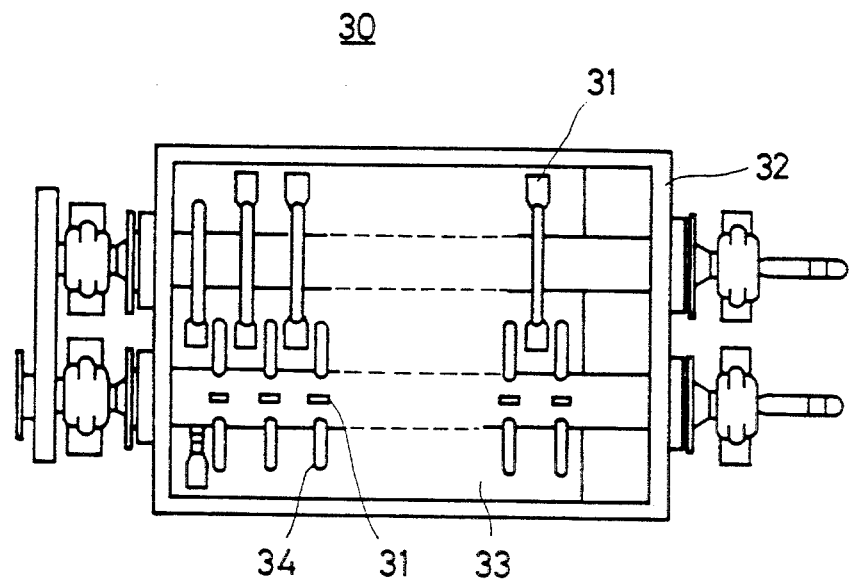
FIG. 3 is an illustration of a kneader-type dryer provided with biaxial rotating blade, with FIG. 3 (a) being a cross-sectional view and FIG. 3 (b) being another cross-sectional view.
Figure 3B:
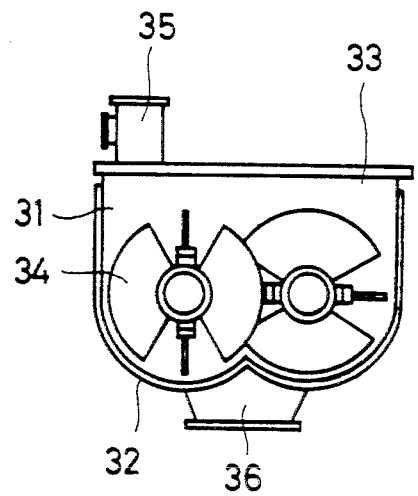

FIGS. 3 (a) and (b) show the dryer 30 of kneader-type provided with uniaxial or biaxial rotating blade 31. Said dryer 30, in which heat-transfer blades 34 and rotating blades 31 are set to rotate in drying chamber 33 surrounded by the jacket 32, can dry Material continuously flowing from inlet 35 at one end to outlet 36 at the other end.

Figure 4:
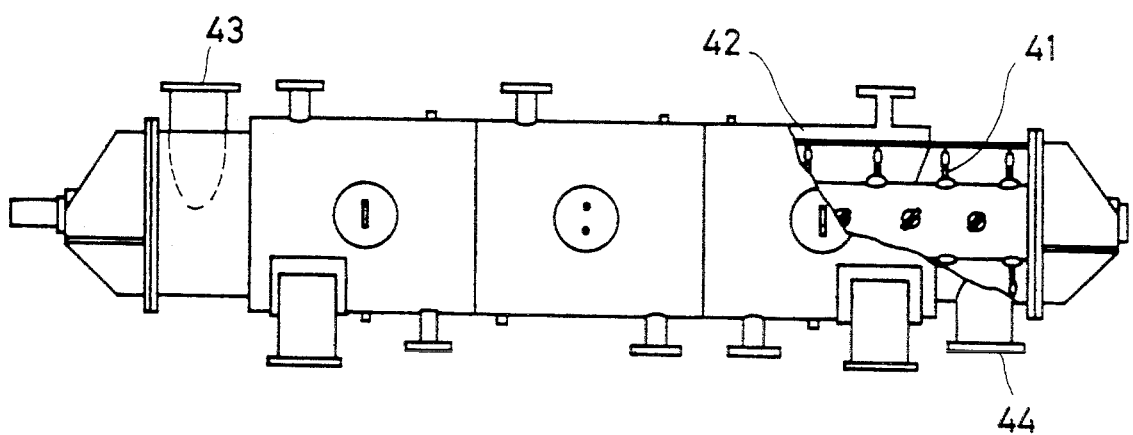
FIG. 4 is an illustration of a single rotor dryer.

FIG. 4 shows the dryer 40 of single rotor-type, in which Material is always agitated by the agitating action of paddle 41 rotating at a high speed in the dryer, and Material is heated to dry by being impacted rapidly against heating jacket 42 by the centrifugal force of said rotation, to be subjected to heat transferred from heating jacket 42 and/or turbulent contact with hot gas. Said dryer 40 can also dry Material continuously flowing from inlet 43 at one end to outlet 44 at the other end.

Figure 5:
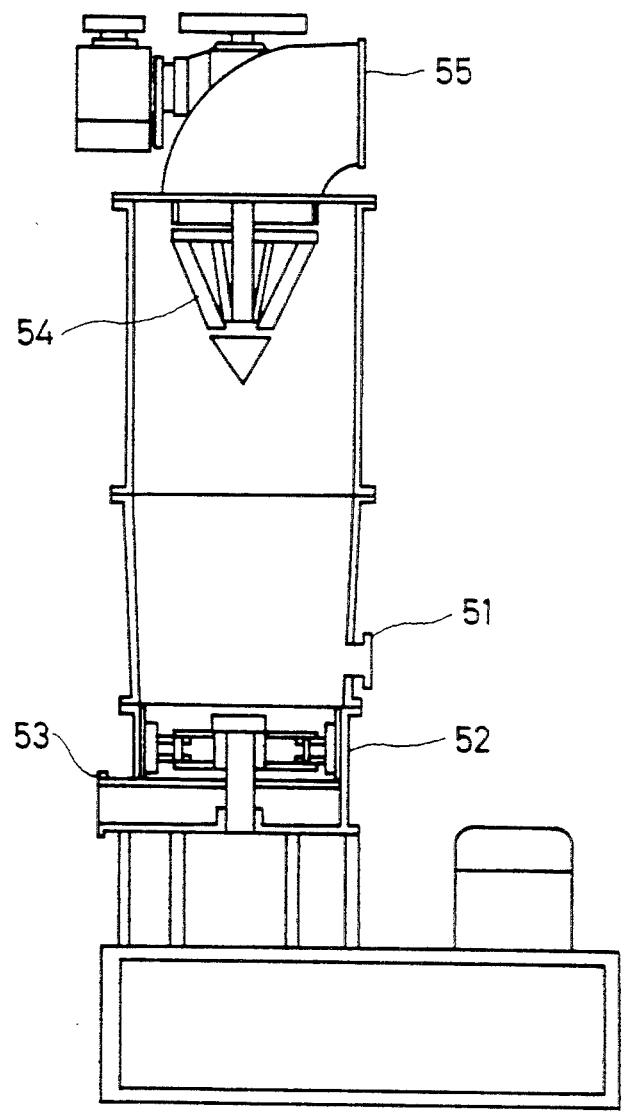
FIG. 5 is an illustration of a micron dryer-type dryer.

FIG. 5 shows dryer 50 of micron dryer type, in which Material is ground and dispersed in the grinding part 52 provided below inlet 51 for supplying Material, and hot air is introduced from inlet for hot air 53 below grinding part 52, that means, grinding and dispersing of Material and rapid heat exchange are effected simultaneously. In said dryer 50 of micron dryer-type, Material after drying is exhausted together with hot air from outlet 55 by way of classifying part 54 in the upper part.

The conditions under which aluminoxane is dried by use of these dryers are appropriately set according to the kind of aluminoxane, the properties of aluminoxane solution due to the methods of preparing aluminoxane, or the kind of the dryer. But, in order to obtain a shearing force sufficient to keep the aluminoxane polydispersive, the preferred shearing force to be applied is usually 0.01 kg/cm$^2$ or greater, more preferably 0.02 to 1 kg/cm$^2$. The proper temperature for drying is usually in the range of 0° to 200° C. preferably 10° to 150° C. Pressure also can be set optionally, but drying under atmospheric pressure to reduced pressure will improve the efficiency of drying.

Herein said solid-state polydispersoids mean those in a dispersive form such as powders or flakes, and more preferably powders having uniform particle diameters.

The aluminoxane thus obtained is in the form of a uniform powder, and when used as the catalyst for production of polymers (that is, polymerization of polymerizable monomers), it shows a favorable solubility and activity, and accordingly, can improve the efficiency in polymerization of monomers. In addition, if aluminoxane is dried in the drying process, so as to be a solid-state polydispersoid, it can be prevented from adhering to the inner wall of the tank or the agitating blade of the dryer, and the yield of aluminoxane will be improved. Further, the drying step can be simplified, since no specific inert gas or solvent is required, and thus the cost for drying can be reduced.

When used as a component of the catalyst in production of various polymers including polyolefins such as polyethylene and polypropylene, or styrene polymers (vinyl aromatic polymers), the aluminoxane obtained in the process of the present invention can improve the yield of these polymers.

As the other catalytic components in the production of these polymers, usual ones can be used. Particularly in the production of styrene polymers, if titanium compound is used with the above-mentioned aluminoxane, especially, methylalumimoxane as a component of the catalyst, styrene polymers having a high syndiotactic configuration as disclosed in Japanese Patent Application Laid-Open No. 104818/1987 can be obtained.

Typical examples of these titanium compounds are those represented by the general formula:

TiR$^2$XYZ wherein R$^2$ is a cyclopentadienyl group, a substituted cyclopentadienyl group or an indenyl group, X, Y, and Z are independently an alkyl group having 1 to 12 carbon atoms, an alkoxyl group having 1 to 12 carbon atoms, an aryl group having 6 to 12 carbon atoms, an aryloxyl group having 6 to 20 carbon atoms, an arylalkyl group having 6 to 20 carbon atoms, or a halogen atom, and the condensed titanium compounds represented by the general formula:

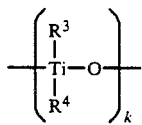

wherein $R^3$ and $R^4$ are each a halogen atom, an alkoxyl group having 1 to 20 carbon atoms, or an acyloxyl group having 1 to 20 carbon atoms, and k is a number of 2 to 20.

In addition, various titanium compounds including titanium tetrachloride, and tetraethoxy titanium can be used. Further, these titanium compounds can be used as complexes with esters, ethers and the like. Depending on the kind of polymers and the polymerization conditions, other kinds of catalyst, for example, organic zirconium compounds can be used.

Therein the high syndiotactic configuration in the styrene polymer means that the polymer has a stereostructure with a configuration that is highly syndiotactic, that is, the stereostructure in which phenyl groups or substituted phenyl groups as side chains are located alternately at opposite directions relative to the main chain consisting of carbon-carbon bonds (racemic modification). The tacticity is quantitatively determined by the nuclear magnetic resonance method using carbon isotope ($^{13}$C-NMR method). The tacticity determined by the $^{13}$C-NMR method can be indicated in terms of proportions of structural units continuously connected to each other, i.e., a diad in which two structural units are connected to each other, a triad in which three structural units are connected to each other, or pentad in which five structural untis are connected to each other. "Styrene polymers having a high syndiotactic configuration" of the present invention include poly(alkylstyrene) such as polystyrene, poly(p-methylstyrene), and poly(m-methylstyrene); poly(halogenated styrene) such as poly(p-chlorostyrene); poly(alkoxystyrene), and styrene copolymers such as styrene-p-methylstyrene copolymer and the like, having such a syndiotacticity that the proportion of racemic diad is at least 75% and preferably at least 85%, of the proportion of racemic pentad is at least 30% and preferably at least 50%.

The styrene polymers produced by the present invention generally have a weight average molecular weight of 5,000 or more, preferably 10,000 to 20,000,000, and a number average molecular weight of 2,500 or more, preferably 5,000 to 10,000,000, and have a high syndiotacticity as described above. After polymerization, if the resulting polymer is subjected to deashing treatment with a washing solution containing hydrochloric acid, etc., and after washing and drying under reduced pressure, further washing with a solvent such as methyl ethyl ketone to remove soluble components and then treating the resulting insoluble components by use of chloroform, etc., depending on necessity, then high purity styrene polymers having an extremely high syndiotacticity can be obtained.

The above-mentioned styrene polymers having a high syndiotactic configuration can be obtained, for example, by polymerizing a styrene monomer (corresponding to the desired styrene polymer, including styrene and styrene derivatives) with a catalyst comprising the above-mentioned titanium compound and the aluminoxane obtained by drying according to the process of the present invention, in the presence or absence of an inert hydrocarbon solvent.

As a catalyst, the aluminoxane can be used singly, or in combination with said organoaluminum compound or with other organometallic compounds, or can be used in the deposited or adsorbed form on an inorganic substance, etc.

The amounts of the abovementioned titanium compounds and the aluminoxane are not determined unconditionally but optionally set depending on the types of styrene or styrene derivatives as the starting material and the types of the catalyst component and other conditions. Usually, the ratio of aluminum/titanium (molar ratio) is in the range of 1 to $10^6$, preferably 10 to $10^4$. As the catalyst, also other catalyst components may be added.

In producing the abovementioned styrene polymers having a high syndiotactic configuration, various methods including bulk polymerization, solvent polymerization and suspension polymerization can be employed. Solvents to be used in the polymerization are aliphatic hydrocarbons such as pentane, hexane, and heptane, alicyclic hydrocarbons such as cyclohexane, and aromatic hydrocarbons such as benzene, toluene, and xylene.

The reaction temperature at the said polymerization is not critical and generally it is set to a temperature of 0° C. to 100° C., preferably 10° C. to 70° C. The period of polymerization is five minutes to 24 hours, preferably one hour or longer.

To control the molecular weight of resulting styrene polymers, it is effective to perform polymerization in the presence of hydrogen.

As described above, according to the process for drying aluminoxane of the present invention, the aluminoxane powder to be obtained is uniform and easy to treat, and is excellent in solubility and activity when used as the catalyst for producing polymers.

If said aluminoxane is dried so as to be a solid-state polydispersoid, adhesion of aluminoxane to the inner wall of the tank, agitating blade or other parts in the dryer is prevented, to improve the yield of aluminoxane. Furthermore, since such drying requires no specific inert gas or solvent, the drying procedure can be simplified, and the cost for drying can be reduced.

According to the process for producing polymers in the present invention, the efficiency in producing polymer can be remarkably improved.

Consequently, the process in the present invention has a very high value for practical use as a process for producing aluminoxane powder efficiently in industrial scale, and as a process for producing polymer in a high yield.

The present invention is described in greater detail with reference to the following examples and comparative examples.

EXAMPLE 1

(1) Preparation of Methylaluminoxane

In a reactor having a capacity of 500 L (L=liter) in which the air was replaced with nitrogen, 20 L of toluene, 17.7 kg (71mol) of copper sulfate ($CuSO_4.5H_2O$) were placed, and 24 L (250 mol) of trimethylaluminum was added at 5° C. over one hour, and the resulting mixture was heated to 40° C. and reacted for eight hours.

Then the solid portion was removed, and the resulting solution was transferred to the dryer provided with a double helical ribbon blade illustrated in FIG. 1, and subjected to agitation at 50° C., and thus toluene was distilled away.

When the viscosity rose, and the torque necessary for agitation increased, the temperature was raised to 110° C., to keep drying until no distillate was observed. As the result, 6.7 kg of methylaluminoxane powder as a reaction product was obtained.

(2) Polymerization of Ethylene

In an autoclave having a volume of 1 L in which the air was replaced with nitrogen, 400 ml of toluene and 1 mmol (as aluminum atom) of methylaluminoxane obtained in above (1), and 5 μmol of bispentamethylcyclopentadienylzirconium dichloride were added successively, and the mixture was heated to 80° C.

Subsequently, ethylene was introduced continuously into the autoclave, and subjected to a polymerization reaction under 8 kg/cm$^2$ for one hour. After the reaction, methanol was added to decompose the catalyst, and then dried to obtain 130 g of polyethylene. The polymerization activity in the above process was 285 kg/g-Zr.

(3) Polymerization of Styrene

In an autoclave having a capacity of 1 L in which the air was substituted with nitrogen, 400 ml of styrene and 4 mmol of triisobutylaluminum, 4 mmol (as aluminum atom) of methylaluminoxane obtained in above (1), and 20 μmol of pentamethylcyclopentadienyltitanium trimethoxide were added successively, and polymerized at 70° C. for one hour.

After completion of the reaction, the resulting product was washed with a mixture of hydrochloric acid and methanol, to separate and remove the catalyst component away, dried to obtain 102.1 g of polystyrene. The syndiotacticity of said polystyrene in terms of racemic pentad was 97% according to the determination by $^{13}$C-NMR method. The results are shown in Table 1.

COMPARATIVE EXAMPLE 1

(1) Preparation of Methylaluminoxane

A solution was prepared in the same manner as in Example (1), and after removal of solid matter, said solution was transferred to a dryer in which the agitating blade is anchor-type, and then toluene was distilled away while agitating at 50° C., but the viscosity was raised and methylaluminoxane was solidified.

The temperature was further raised to 110° C., and drying was continued until no distillation was observed. As the result, 8.0 kg of a solid in flake form containing the methylaluminoxane and residual toluene was obtained.

(2) Polymerization of Ethylene

Ethylene was polymerized in the same manner as in Example 1 (2) except that methylaluminoxane obtained in (1) above was used as aluminoxane, to obtain 84 g of polyethylene. The polymerization activity in that process was 184 kg/g-Zr.

(3) Polymerization of Styrene

Styrene was polymerized in the same manner as in Example 1 (3) except that methylaluminoxane obtained in (1) above was used as aluminoxane, to obtain 91.4 g of polystyrene. The results are shown in Table 1.

EXAMPLE 2

(1) Preparation of Methylaluminoxane

A solution was prepared in the same manner as in Example 1 (1). After removal of the solid portion, the solution was transferred to the dryer with a rotating screw-type agitating blades orbiting in a conical tank illustrated in FIG. 2, and agitated at 50° C. to distillate toluene away.

When the viscosity of the solution rose, and the torque necessary for agitation increased, the temperature was raised to 110° C., and drying was continued until no distillation was observed. As the result, 6.8 kg of methylaluminoxane powder as reaction product was obtained.

(2) Polymerization of Ethylene

The procedure of Example 1 (2) was repeated except that methylaluminoxane obtained in (1)above was used as aluminoxane, to obtain 129 g of polyethylene. The polymerization activity then was 283 kg/g-Zr.

(3) Polymerization of Styrene

Styrene was polymerized in the same manner as in Example 1 (3) except that methylaluminoxane obtained in (1)above was used as aluminoxane, to obtain 101.2 g of polystyrene.

The results are shown in Table 1.

EXAMPLE 3

The procedure of Example 1 was repeated except that aluminoxane solution was dried in the kneader-type dryer provided with biaxial rotating blade illustrated in FIG. 3, to obtain aluminoxane, polyethylene and polystyrene. The results are shown in Table 1.

EXAMPLE 4

The procedure of Example 1 was repeated except that aluminoxane solution was dried in the single rotor dryer illustrated in FIG. 4, to obtain aluminoxane, polyethylene and polystyrene. The results are shown in Table 1.

EXAMPLE 5

The procedure of Example 1 was repeated except that aluminoxane solution was dried in the micron dryer-type dryer illustrated in FIG. 5, to obtain aluminoxane, polyethylene and polystyrene.

The results are shown in Table 1.

TABLE 1

| | Dryer | Total yield (kg) | Yield of polyethylene (g) | Yield of SPS* (g) |
|---|---|---|---|---|
| Example 1 | Double helical blade | 6.7 | 130 | 102.1 |
| Comparative Example 1 | Anchor-type blade | 8.0 | 84 | 91.4 |
| Example 2 | Screw-type agitating blade | 6.8 | 129 | 101.2 |
| Example 3 | Kneader-type | 7.0 | 131 | 104.2 |
| Example 4 | Single rotor-type | 6.9 | 128 | 103.5 |
| Example 5 | Micron dryer-type | 6.8 | 124 | 101.8 |

*syndiotactic polystyrene

What is claimed is:

1. A process for drying aluminoxane, which comprises drying a viscous solution containing aluminoxane, while applying a sufficient shearing force to keep said viscous solution in a polydispersive state, so as to make a dispersion of dry particulate aluminoxane.

2. The process according to claim 1, wherein the shearing force to be applied is 0.01 kg/cm² or greater.

3. The process according to claim 1, wherein the shearing force to be applied is 0.02 to 1 kg/cm².

4. The process according to claim 1, wherein aluminoxane is methylaluminoxane.

5. The process of claim 1, wherein the aluminoxane comprises a repeating unit represented by the formula:

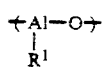

wherein $R^1$ is an alkyl group having 1-8 carbon atoms.

6. The process of claim 5, wherein the aluminoxane is formed by contacting an organoaluminum compound of the formula:

$$AlR^1_3$$

wherein $R^1$ is $C_1$-$C_8$ alkyl, with water as a condensing agent.

7. In a process for producing polymers, which comprises polymerizing a polymerizable monomer in the presence of a catalyst, the improvement comprising using the aluminoxane obtained according to the process of claim 1 as a component of the catalyst.

8. The process according to claim 5, wherein the polymer is an olefin polymer or a styrene polymer.

9. The process according to claim 6, wherein the styrene polymer is a styrene polymer having high syndiotactic configuration.

10. The process of claim 5, wherein the aluminoxanes comprise a repeating unit represented by the formula:

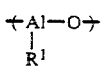

wherein $R^1$ is an alkyl group having 1-8 carbon atoms.

11. The process of claim 10, wherein the aluminoxane is formed by contacting an organoaluminum compound of the formula:

$$AlR^1_3$$

wherein $R^1$ is $C_1$-$C_8$ alkyl, with water as a condensing agent.

* * * * *